(12) United States Patent
Chen et al.

(10) Patent No.: US 10,694,989 B2
(45) Date of Patent: Jun. 30, 2020

(54) INTELLIGENT STOP SHAKING DEVICE, SYSTEM AND METHOD

(71) Applicants: Robert C V Chen, Cupertino, CA (US); Tiffany Y W Chen, Cupertino, CA (US)

(72) Inventors: Robert C V Chen, Cupertino, CA (US); Tiffany Y W Chen, Cupertino, CA (US)

( * ) Notice: Subject to any disclaimer, the term of this patent is extended or adjusted under 35 U.S.C. 154(b) by 0 days.

(21) Appl. No.: 16/458,998

(22) Filed: Jul. 1, 2019

(65) Prior Publication Data
US 2019/0388019 A1  Dec. 26, 2019

Related U.S. Application Data

(63) Continuation-in-part of application No. 16/006,830, filed on Jun. 12, 2018, now abandoned.

(51) Int. Cl.
*A61B 5/00* (2006.01)
*A61B 5/11* (2006.01)
(Continued)

(52) U.S. Cl.
CPC .......... *A61B 5/4082* (2013.01); *A61B 5/1101* (2013.01); *A61B 5/6825* (2013.01);
(Continued)

(58) Field of Classification Search
CPC ....... A61B 5/4082; A61B 5/1101; A61B 5/11; A61B 5/067; A61B 5/6825; A61B 5/6828;
(Continued)

(56) References Cited

U.S. PATENT DOCUMENTS

| | | | |
|---|---|---|---|
| 6,422,992 B1 * | 7/2002 | Raffel | A61M 21/00 600/27 |
| 6,730,049 B2 * | 5/2004 | Kalvert | A61F 5/0118 600/545 |

(Continued)

FOREIGN PATENT DOCUMENTS

WO  WO-2016102958 A1 *  6/2016  ....... A63B 21/00192

OTHER PUBLICATIONS

Top2D3D (Aug. 16, 2017). "iStopShaking devices to Stop Parkinson's disease" https://www.youtube.com/watch?v=kgRgcmiS-vl (Year: 2017).*

*Primary Examiner* — Justine R Yu
*Assistant Examiner* — Matthew R Moon
(74) *Attorney, Agent, or Firm* — Lyman Moulton, Esq.; Moulton Patents, PLLC

(57) ABSTRACT

A system for inhibiting shaking includes multiple parallel tracks each to join a plurality of mini gyroscopes (MG) in series, the parallel tracks joined at one or more control junctures and disposed on a flexible substrate wrap. The system includes multiple MG accumulated in series in the parallel tracks via a user's action(s), the MG configured to spin 90 degrees relative to each other and a single parallel track at a magnitude and a direction of relative angular velocities. The system additionally includes mini accelerometers and a digital processing circuit to differentiate shaking and purposeful movement via a first and a second derivative of accelerations of portions of the flexible substrate wrap. The system further includes a microcontroller to control the variable angular momentum and the spin axis of the MG to ablate shaking relative to purposeful movement of portions of the substrate wrap.

19 Claims, 15 Drawing Sheets

(51) Int. Cl.
*A61B 5/06* (2006.01)
*A61H 23/00* (2006.01)

(52) U.S. Cl.
CPC .............. *A61B 5/067* (2013.01); *A61B 5/486* (2013.01); *A61B 5/6822* (2013.01); *A61B 5/6828* (2013.01); *A61B 2562/0219* (2013.01); *A61H 23/00* (2013.01); *A61H 2201/5084* (2013.01)

(58) Field of Classification Search
CPC .......... A61B 2562/0219; A61B 5/6822; A61B 5/486; A61H 1/00; A61H 1/02; A61H 1/0285; A61H 1/0288; A61H 1/0296; A61H 1/008; A61H 2201/0157; A61H 1/0173; A61H 1/018; A61H 1/12; A61H 1/1666; A61H 1/1673; A61H 1/5053; A61H 1/5071; A61H 2230/04; A61H 2230/06; A61H 2230/50; A61H 2230/505; A61H 2205/04; A61H 2205/065; A61H 2205/067; A61H 2205/10; A61H 2205/106; A61H 2205/12; A61H 7/001
See application file for complete search history.

(56) References Cited

U.S. PATENT DOCUMENTS

| | | | |
|---|---|---|---|
| 2003/0006357 A1* | 1/2003 | Kaiser | F16F 7/1005 248/550 |
| 2009/0005713 A1* | 1/2009 | Podrazhansky | A61H 23/0236 601/2 |
| 2013/0303951 A1* | 11/2013 | Liu | A61H 23/00 601/46 |
| 2017/0188895 A1* | 7/2017 | Nathan | A61B 5/1122 |

* cited by examiner

INTELLIGENT STOP SHAKING DEVICE, SYSTEM AND METHOD

CROSS-REFERENCE TO RELATED APPLICATIONS

This application claims the benefit of the priority date of earlier filed U.S. Non-Provisional Utility application Ser. No. 15/446,552 filed Mar. 22, 2017 and U.S. Non-Provisional Utility application Ser. No. 16/006,830 filed Jun. 12, 2018 both for Robert CV Chen and Tiffany YW Chen each incorporated herein by reference in its entirety.

BACKGROUND OF THE INVENTION

Parkinson's disease is a medical disorder whose primary symptom is excessive muscle contraction manifest by shaking. It is characterized by muscle rigidity, a slowing of physical movements, and in many cases tremor. At its worst, it can affect every muscle system in the body.

Parkinson's disease is a progressive, neurodegenerative disorder that affects movement, muscle control, and balance as well as numerous other functions. It is part of a group of conditions known as motor systems disorders. Parkinson's disease was named for James Parkinson, a general practitioner in London during the 19th century who first described the symptoms of the disease. Symptoms describing Parkinson's disease are mentioned in the writings of medicine in India dating back to 5,000 BCE as well as in Chinese writings dating back approximately 2500 years. Parkinson's disease is the most common movement disorder and the second most common neurodegenerative disorder, the most common being Alzheimer's disease.

Parkinson's disease has an insidious onset, meaning it is slow to progress. The common early stage symptom is a tremor and an awkward movement: maximal when the limb is at rest and disappearing with voluntary movement and sleep. It affects to a greater extent the most distal part of the limb and at onset it typically appears in only a single arm or leg, becoming bilateral later. The major symptoms are a rest tremor, bradykinesia, muscle rigidity and posture gait disorder.

Adult-Onset Parkinson's Disease—This is the most common type of Parkinson's disease. The Parkinson's disease can significantly impair quality of life not only for the patients but for their families as well, and especially for the primary caregivers.

According to the American Parkinson's Disease Association, there are approximately 1.5 million people in the U.S. who suffer from Parkinson's disease—approximately 1-2% of people over the age of 60 and 3-5% of the population over age 85. The incidence of PD ranges from 8.6-19 per 100,000 people. Approximately 50,000 new cases are diagnosed in the U.S. annually. There are more than 2.0 million people in China who suffer from Parkinson's disease.

There has therefore been a long unsatisfied demand in the market place for a device, system and method of inhibiting shaking for Parkinson's victims.

SUMMARY OF THE INVENTION

A disclosed device and system for inhibiting shaking comprises a plurality of parallel tracks comprising semi rigid connective material similar to cartilage on a flexible substrate wrap, the parallel tracks configured to provide a semi rigid route and inter placement of a plurality of devices received therein. The parallel tracks each configured to join mini gyroscope devices accumulated in series at any point on each of the parallel tracks, the mini gyroscopes configured to be routed along a single parallel track and be accumulated by an accumulating movement of a hand, leg or neck. The tracks are joined at one or more control junctures and disposed on a flexible substrate wrap. The mini gyroscopes are configured to spin about an axis relative to a single parallel track at a variable angular momentum. The system additionally includes a plurality of accelerometers inter placed between the mini gyroscopes in the parallel tracks configured to differentiate shaking and purposeful movement of portions of the flexible substrate wrap and provide output thereof and feedback on shaking ablation. The system further includes a controller configured to control the variable angular momentum and the spin axis of the mini gyroscopes to ablate shaking relative to purposeful movement of portions of the substrate wrap based on accelerometer output.

A disclosed method for an inhibition of shaking, the method comprises providing a plurality of parallel tracks each configured to join a plurality of mini gyroscopes in series, the parallel tracks joining one or more control junctures disposed on a flexible substrate wrap. The method also comprises providing a plurality of mini gyroscopes spaced apart in series by each of the plurality of parallel tracks, the mini gyroscopes spinning about an axis relative to a single parallel track at a variable angular momentum. Additionally, the method includes providing a plurality of accelerometers for differentiating shaking and purposeful moving of portions of the flexible substrate wrap and providing output thereof and feedback on shaking ablation. The method further includes providing a controller controlling the variable angular momentum and the spin axis of the mini gyroscopes to ablate shaking relative to purposeful movement of portions of the substrate wrap based on accelerometer output.

Other aspects and advantages of embodiments of the disclosure will become apparent from the following detailed description, taken in conjunction with the accompanying drawings, illustrated by way of example of the principles of the disclosure.

Figure 1:
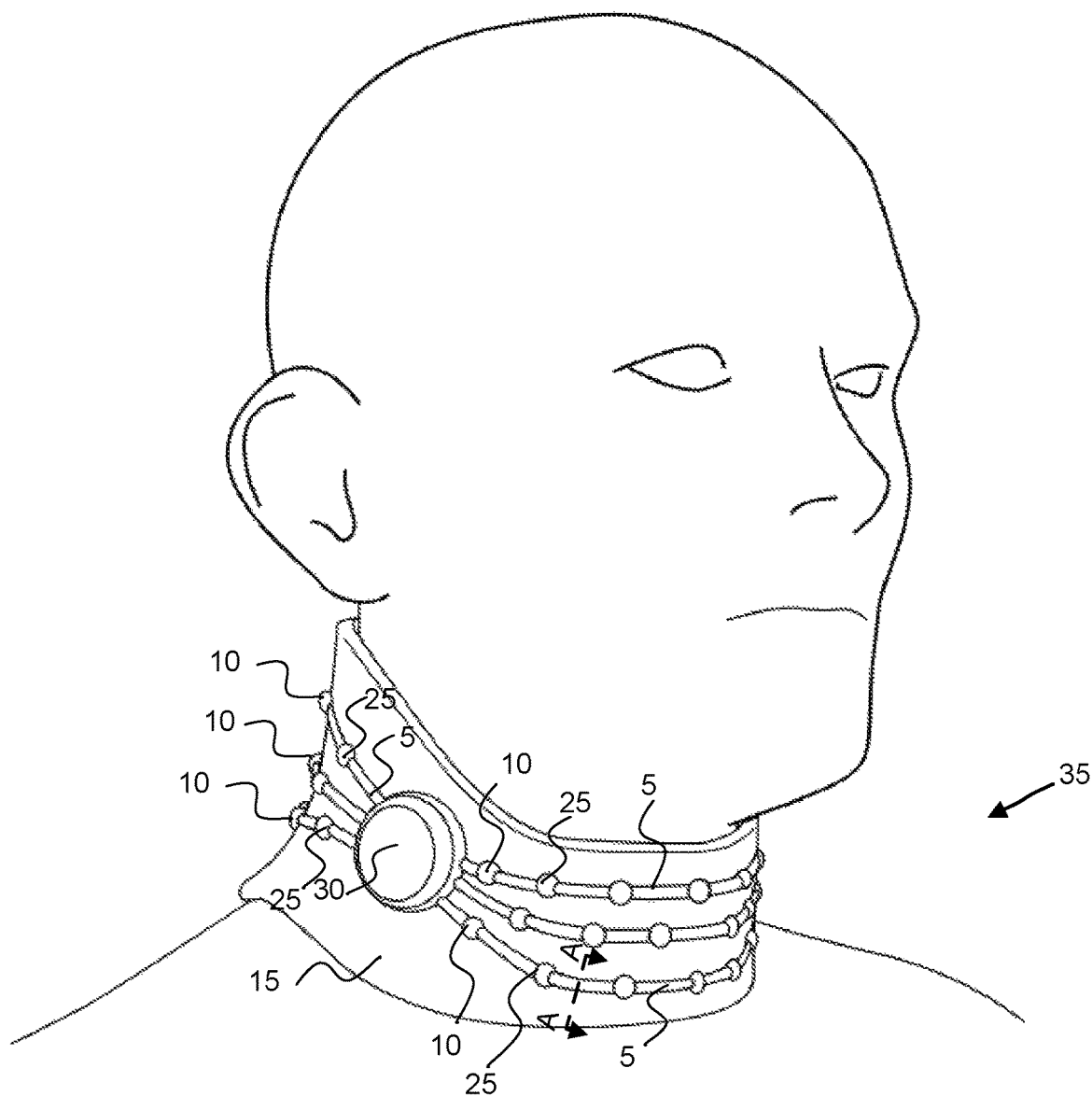
FIG. 1 is a back perspective view of the intelligent stop shaking necklace device and system in accordance with an embodiment of the present disclosure.

Throughout the description, same reference numbers may be used to identify same or similar elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of the invention.

Throughout the present disclosure, the term 'ablate' refers to inhibiting, attenuating, lessening or countering shaking by mechanical means. The ablation of shaking may not remove the shaking but allow a user of the disclosure to have more purposeful use of their fingers, neck, legs, ankles, etc. The term 'track' refers to a connective physical structure for providing a common rigid route and inter placement of the mini gyroscopes and accelerometers onto the substrate glove, bracelet/choker or anklet. The track therefore accumulates and channels the angular momentum for the fingers and thumb of a user's hand. The term 'shaking' referred to in the present disclosure is synonymous with trembling and spasmodic movement associated with neurological seizures. The term 'parallel' refers to multiple tracks that never intersect and may diverge. The term 'accumulate' refers to gather together in each track an increasing number of devices in the tracks at any area via a purposeful shaking of the device. Cartilage refers to a firm, touch, elastic and fibrous flexible connective material.

Dimensions detailed herein and in the drawings are intended to be a guide to nominal manufacturing dimensions. The detailed dimensions may vary by plus or minus ten percent taking into account manufacturing restraints and materials for various embodiments as recited, taught and suggested herein. The dimensions therefore are applicable to at least one embodiment but are not meant to be limiting to other embodiments of the disclosure.

Each iStopShaking® Device is powered by 25 to 30 mini gyroscopes (spinning at up to 40,000 rpm) per gyroscope. The gyroscopes are driven by long life battery. The mini gyroscopes are driven by a brushless DC (BLDC) driver controller. The BLDC drives one or more brushless slot less DC motors. The speed of the brushless slot less DC motor is up to 70,000 rpm and the torque is up to 48 mNm.

The controller board user interface is touch sensing buttons, I/O, oscillator, timer, motion detection sensor. The iStopShaking device works in conjunction with the gyroscope and the Accelerometer. The accelerometer is designed to measure non-gravitational acceleration. When the iStopShaking device is integrated with the accelerometer, it goes from a standstill to any velocity. The Accelerometer is designed to respond to the vibrations associated with such movement. It uses microscopic crystals that go under stress when vibrations occur, and from that stress a voltage is generated to create a reading on any acceleration. Accelerometers are important components to devices that track fitness and other measurements in the quantified self-movement.

Components of the disclosed iStopShaking™ devices are, On-off switch, High-Low intensity switch, sleep mode, Wireless CPU chip & Bluetooth connects with iStopShaking device with iPhone APP, iStopShaking® will also monitor eight activities and send data to patient's LCD screen on wrist and thru wireless connectivity thru wireless chip and Bluetooth to user's iPhone.

The iStopShaking devices also measure a broad range of vital signs, store/transmit data and sync with smartphones, tablets and PCs. iStopShaking devices has Built in sensors that will monitor and Measure heart rate, Blood oxygen sensor, Skin temperature sensor, Sleep sensor, Calories expended sensor, Exercise, steps, walk distance sensor, and Exposure to radiation.

Each iStopShaking® device contains between 24 to 30 mini gyroscopes and accelerometers connected to "multiple tracks constructed inside hollow tube(s)". The gyroscopes are connected in tracks built inside hollow tubes. Five hollow tubes with up to 30 gyroscopes are connected to brushless controller and brushless slot less DC compact motors. The brushless slot less DC compact motors have high acceleration, low noise and are connected to a power management (battery power source).

A gyroscope is a device that uses Earth's gravity to help determine orientation. Its design consists of a freely-rotating disk called a rotor, mounted onto a spinning axis in the center of a larger and more stable wheel.

The accelerometers measure acceleration i.e. how fast the gyroscope are speeding up or slowing down. Triaxial Accelerometers are used to sense both static (e.g. gravity) and dynamic (e.g. sudden starts/stops) acceleration along three Cartesian axis. The accelerometer is used for tilt-sensing. An accelerometer is also used to sense gyroscope motion. Accelerometers will have a digital interface connected to wireless CPU with Bluetooth. The quantified-self movement build into the iStopShaking® device allow individuals to track all aspects of their daily lives, including their total activity, number of steps, food they eat, amount of sleep, heart rate, and mood.

FIG. 1 is a back perspective view of the intelligent stop shaking necklace device and system in accordance with an embodiment of the present disclosure. The disclosed shaking inhibiting device 35 comprises a plurality of mini gyroscopes (MG) 10 spaced apart in series by each of a plurality of parallel tracks 5, the mini gyroscopes 10 configured to spin about an axis relative to a single parallel track 5 at a variable angular momentum. The device 35 also includes a plurality of mini accelerometers (MA) 25 configured to differentiate shaking and purposeful movement of portions of the flexible substrate wrap 15 and provide output thereof and feedback on shaking ablation. The device further includes a controller 30 configured to control the variable angular momentum and the spin axis of the mini gyroscopes to ablate shaking relative to purposeful movement of portions of the substrate wrap 15 based on the accelerometer output.

The mini gyroscopes 10 and the accelerometers 25 are depicted similarly from an outside appearance because placement and respective quantity may be determined by medical or technical personnel depending on the degree of sensitivity and control needed for the user and patient. In other words, more distributed accelerometer placement enables better determination of the purposeful and involuntary movement a patient suffers and therefore also allows better management and control of shaking ablation.

The parallel tracks 5 may be comprised of a semi rigid connective material similar to cartilage and therefore channel the angular momentum of the no shake gyroscopes. The tracks may be circular as in a bracelet, a necklace or an anklet or the tracks may be phalangeal as in the back of each finger and thumb. The tracks may therefore originate at bidirectional control junctures as in the bracelet, necklace and anklet or may originate at a unidirectional control juncture as at a back of a wrist for a hand glove application. The tracks may also therefore terminate at bidirectional control junctures or at the ends of fingers and a thumb respectively.

Electric power for the MG 10 and the MA 25 resides in lengthwise portions of the track 5 so that the MG 10 and the MA 25 may move through the track 5 and rest in any place along the track or along predetermined grid points in the track according to a track configuration. Also, communication signals run lengthwise in the track along portions thereof to communicate information between the controller 30 and the MG 10 and the MA 25.

Figure 2:
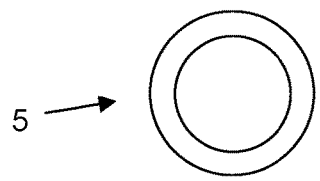
FIG. 2 is a cross sectional view of A-A shown in FIG. 1 in accordance with an embodiment of the present disclosure.

FIG. 2 is a cross-sectional view of A-A shown in FIG. 1 in accordance with an embodiment of the present disclosure. A track 5 may be hollow and circular as depicted allowing the mini gyroscopes 10 and accelerometers 25 to ride inside the track according to accumulation movements of the flexible substrate wrap 15. A track 5 may also be solid and circular and the mini gyroscopes 10 and accelerometers 25 may ride the track on an outside thereof.

Figure 3:
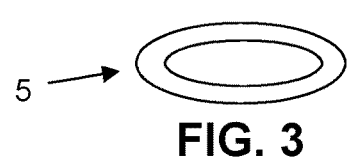
FIG. 3 is a cross-sectional view of A-A shown in FIG. 1 in accordance with an embodiment of the present disclosure.

FIG. 3 is a cross-sectional view of A-A shown in FIG. 1 in accordance with an embodiment of the present disclosure. A track 5 may be hollow and oval as depicted allowing the mini gyroscopes 10 and accelerometers 25 to ride inside the track according to accumulation movements of the flexible substrate wrap 15. A track 5 may also be solid and oval and the mini gyroscopes 10 and accelerometers 25 may ride the track on an outside thereof.

Figure 4:
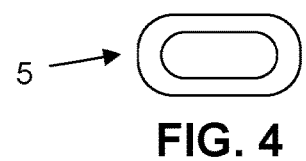
FIG. 4 is a cross-sectional view of A-A shown in FIG. 1 in accordance with an embodiment of the present disclosure.

FIG. 4 is a cross-sectional view of A-A shown in FIG. 1 in accordance with an embodiment of the present disclosure. A track 5 may be hollow and angular as depicted allowing the mini gyroscopes 10 and accelerometers 25 to ride inside the track according to accumulation movements of the flexible substrate wrap 20. A track 5 may also be solid and angular and the mini gyroscopes 10 and accelerometers 25 may ride the track on an outside thereof.

Accumulation movements include purposeful flicking movements of a hand or a leg to shake the mini gyroscopes and the accelerometers to the tips of a user's fingers for example. The mini gyroscopes may also be brought back nearer to a wrist of the user via gravity or taking the flexible substrate wrap off the user and flicking it in a manner to redistribute the mini gyroscopes and accelerometers from the accumulated positions. The accumulation movements are differentiated by other purposeful movements of the user's hand as if the user were trying to flick water from his or her finger tips. Other purposeful movements include writing, gentle washing, squeezing, pointing, etc from most everyday conscious movements. Shaking movements are not conscious movements and are involuntary as a result of disease or deterioration of the nerves and muscles of the body. Bodily functions include heart rate, diastolic and systolic pressures, oxygen content, and relative hormonal components in the blood of a user. Any point of accumulation refers to distances from a controller juncture along a track.

Reference numbers and similar claimed limitations are depicted for the intelligent stop shaking necklace 35 and for a further disclosed anklet and glove. Various views depicted include similar configurations of respective elements. An embodiment of the shaking inhibiting system further comprises a circuit in the controller configured to set an accelerometer acceleration and a spin axis of the mini gyroscopes equal to a an acceleration and a direction of the purposeful movement determined by the accelerometer output during a purposeful movement. The disclosed system further comprises a circuit for differentiation of accelerometer acceleration output from shaking greater than an accelerometer acceleration from purposeful movement.

Returning to FIG. 1, an embodiment of the intelligent stop shaking necklace device and system is disclosed in accordance with an embodiment of the present disclosure. A circuit is included for incorporating feedback on shaking ablation provided by the accelerometers into an increase or a decrease of an intensity of the angular momentum and the spin axis of the mini gyroscopes. A comprised flexible wrap is configured as a substrate for the plurality of mini gyroscopes and the plurality of parallel tracks and one or more control junctures, the substrate and portions thereof comprising a hand glove, a bracelet and an anklet.

Figure 5:
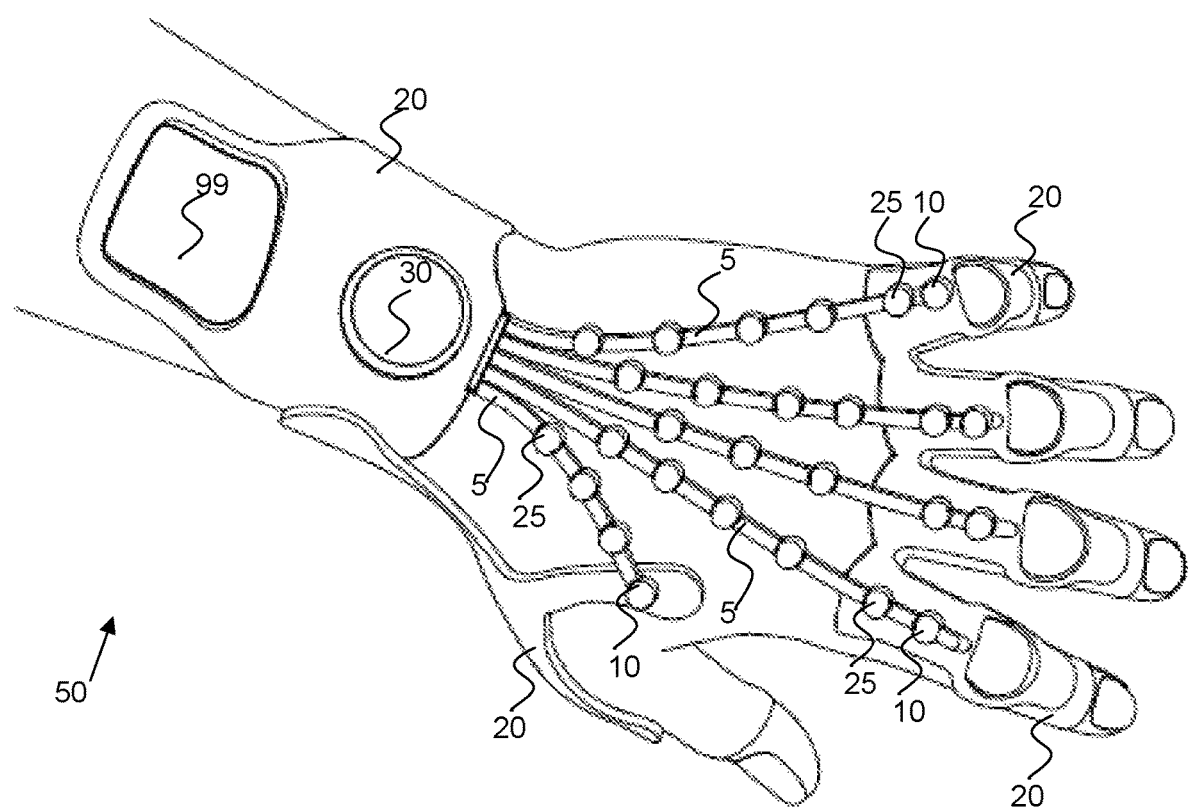
FIG. 5 is a top posterior perspective view of the intelligent stop shaking hand glove device and system in accordance with an embodiment of the present disclosure.

FIG. 5 is a top anterior perspective view of the intelligent stop shaking hand glove device and system in accordance with an embodiment of the present disclosure. The disclosed shaking inhibiting hand glove device 50 comprises a plurality of mini gyroscopes 10 spaced apart in series by each of a plurality of parallel tracks 5, the mini gyroscopes 10 configured to spin about an axis relative to a single parallel track 5 at a variable angular momentum. The device also includes a plurality of accelerometers 25 configured to differentiate shaking and purposeful movement of portions of the flexible substrate wrap 40 and provide output thereof and feedback on shaking ablation. The device further includes a controller 30 configured to control the variable angular momentum and the spin axis of the mini gyroscopes to ablate shaking relative to purposeful movement of portions of the substrate wrap 20 based on the accelerometer output. The controller may function via a press and turn to control a desired amount of shaking ablation. The glove device 50 may yet further include a display screen 99 to communicate with the user and the controller 30.

In another embodiment of the disclosure, an intelligent stop shaking hand glove device and system is disclosed in accordance with an embodiment of the present disclosure. The flexible substrate wrap 20 comprises a hand glove 40 with finger and thumb portions and finger and thumb parallel tracks comprising a control juncture adjacent a wrist of the glove. In an embodiment, at least one controller portion is disposed at one control juncture thereof and another controller portion is disposed at another juncture thereof. An ablation intensity switch is configured to allow a user of the device to determine a mini gyroscope angular momentum from one of a plurality of ablation intensity gradations.

Figure 6:
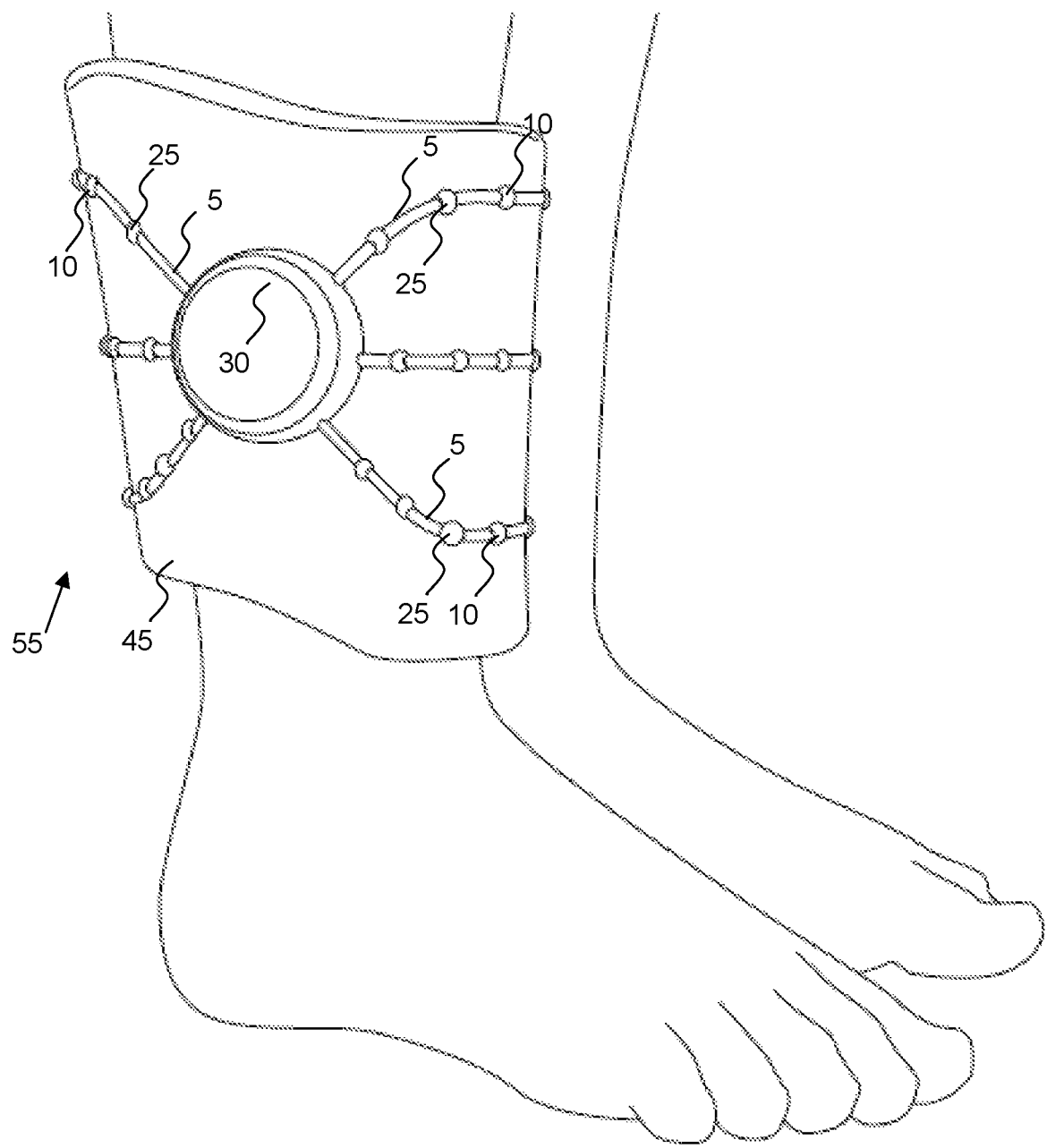
FIG. 6 is a side perspective view of the intelligent stop shaking anklet device and system in accordance with an embodiment of the present disclosure.

FIG. 6 is a side perspective view of the intelligent stop shaking anklet device and system in accordance with an embodiment of the present disclosure. The flexible substrate wrap also comprises an anklet 55 with three parallel tracks configured to circumnavigate an ankle. The flexible substrate wrap 45 is similar in composition to a bracelet with three parallel tracks circumnavigating a neck. The disclosed shaking inhibiting anklet device 55 comprises a plurality of mini gyroscopes 10 spaced apart in series by each of a plurality of parallel tracks 5, the mini gyroscopes 10 configured to spin about an axis relative to a single parallel track 5 at a variable angular momentum. The device also includes a plurality of accelerometers 25 configured to differentiate shaking and purposeful movement of portions of the flexible substrate wrap 45 and provide output thereof and feedback on shaking ablation. The device further includes a controller 30 configured to control the variable angular momentum and the spin axis of the mini gyroscopes to ablate shaking relative to purposeful movement of portions of the substrate wrap 45 based on the accelerometer output.

Figure 7:
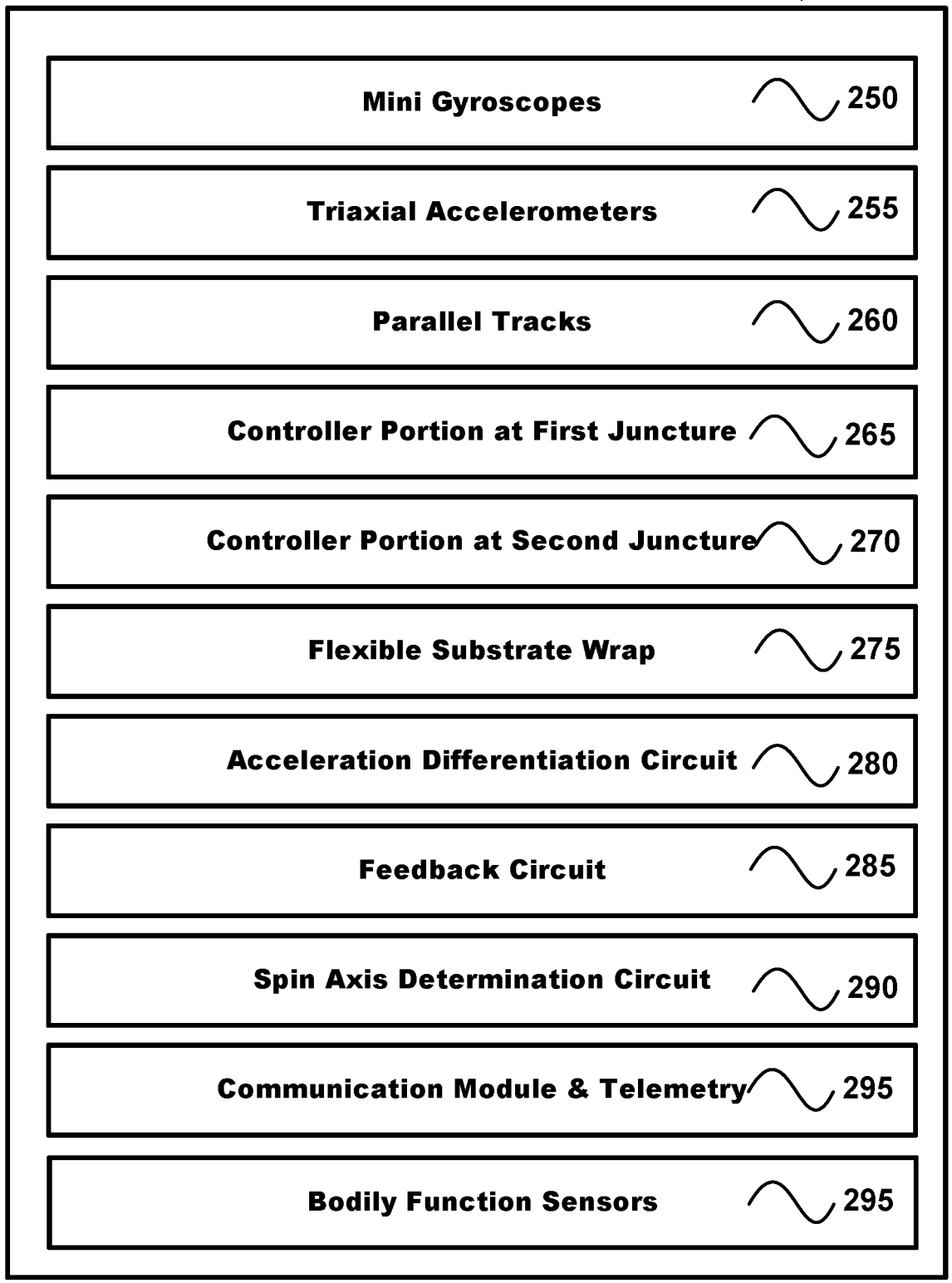
FIG. 7 is a block diagram representation of the intelligent shake inhibiting device and system in accordance with an embodiment of the present disclosure.

FIG. 7 is a block diagram representation of the intelligent shake inhibiting device and system in accordance with an embodiment of the present disclosure. The system includes mini gyroscopes 250, mini accelerometers 255, parallel tracks 260, a controller portion at a first juncture 265, a controller portion at a second juncture 270, a flexible substrate wrap 275, an acceleration differentiation circuit 280, a feedback circuit 285, a spin axis determination circuit 290, a communication module & telemetry 295 and bodily function sensors 295 as disclosed herein.

Figure 8:
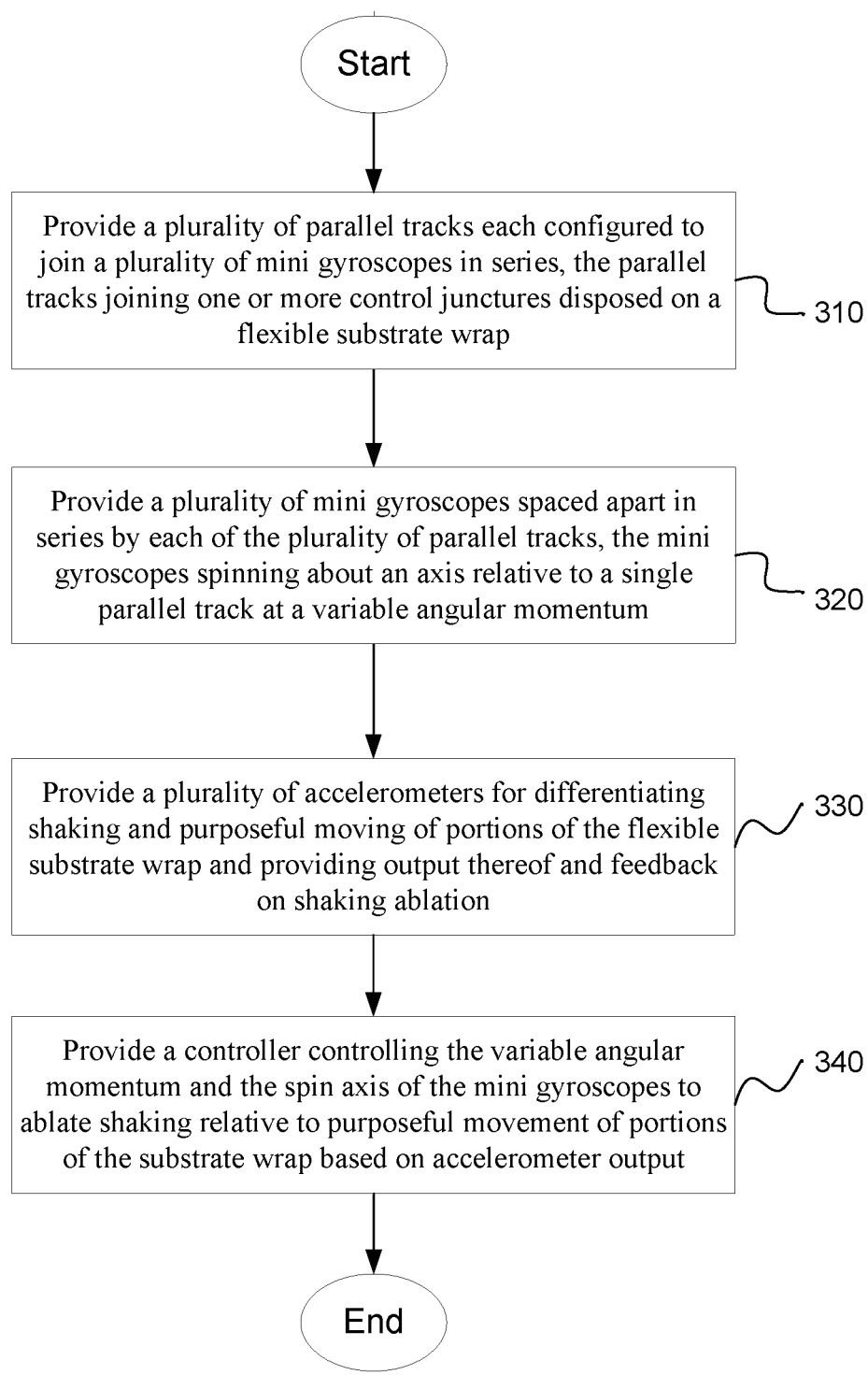
FIG. 8 is a flow chart of a method for intelligently inhibiting shaking in accordance with an embodiment of the present disclosure.

FIG. 8 is a flow chart of a method for intelligently inhibiting shaking in accordance with an embodiment of the present disclosure. The method includes providing 310 a plurality of parallel tracks each configured to join a plurality of mini gyroscopes in series, the parallel tracks joining one or more control junctures disposed on a flexible substrate wrap. The method also comprises providing 320 a plurality of mini gyroscopes spaced apart in series by each of the plurality of parallel tracks, the mini gyroscopes spinning about an axis relative to a single parallel track at a variable angular momentum. Additionally, the method includes providing 330 a plurality of accelerometers for differentiating shaking and purposeful moving of portions of the flexible substrate wrap and providing output thereof and feedback on shaking ablation. The method further includes providing 340 a controller controlling the variable angular momentum and the spin axis of the mini gyroscopes to ablate shaking relative to purposeful movement of portions of the substrate wrap based on accelerometer output.

Figure 9:
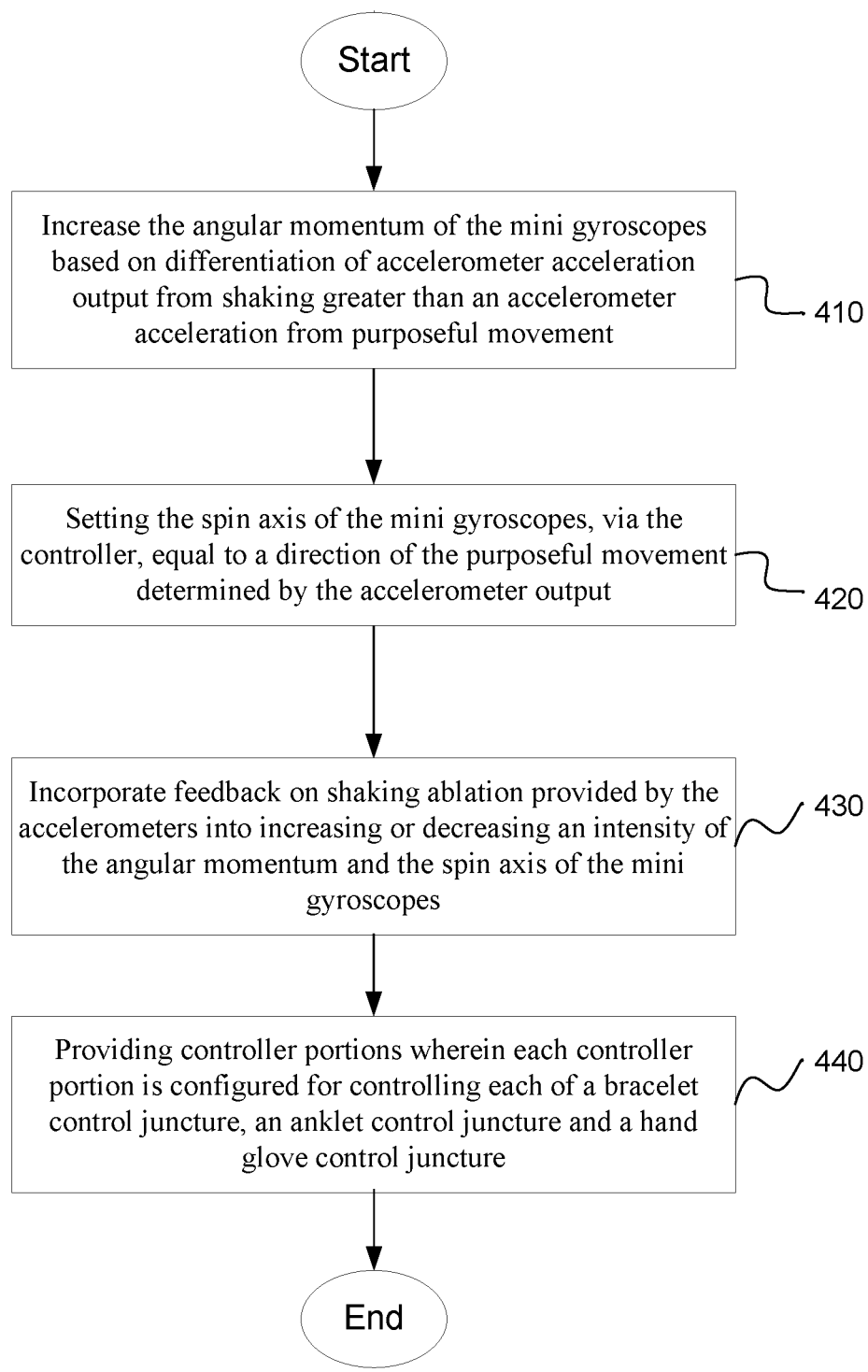
FIG. 9 is a flow chart of implementation methods for intelligently inhibiting shaking in accordance with an embodiment of the present disclosure.

FIG. 9 is a flow chart of implementation methods for intelligently inhibiting shaking in accordance with an embodiment of the present disclosure. The implementation method includes increasing 410 the angular momentum of the mini gyroscopes based on differentiation of accelerometer acceleration output from shaking greater than a mini-accelerometer acceleration from purposeful movement. The implementation method also includes setting 420 the spin axis of the min gyroscopes via the controller equal to a direction of the purposeful movement determined by the accelerometer output. The method additionally includes incorporating feedback 430 on shaking ablation provided by the accelerometers into increasing or decreasing an intensity of the angular momentum and the spin axis of the mini gyroscopes. The method further includes providing 440 controller portions wherein each controller portion is configured for controlling each of a bracelet control juncture, an anklet control juncture and a hand glove control juncture.

Figure 10:
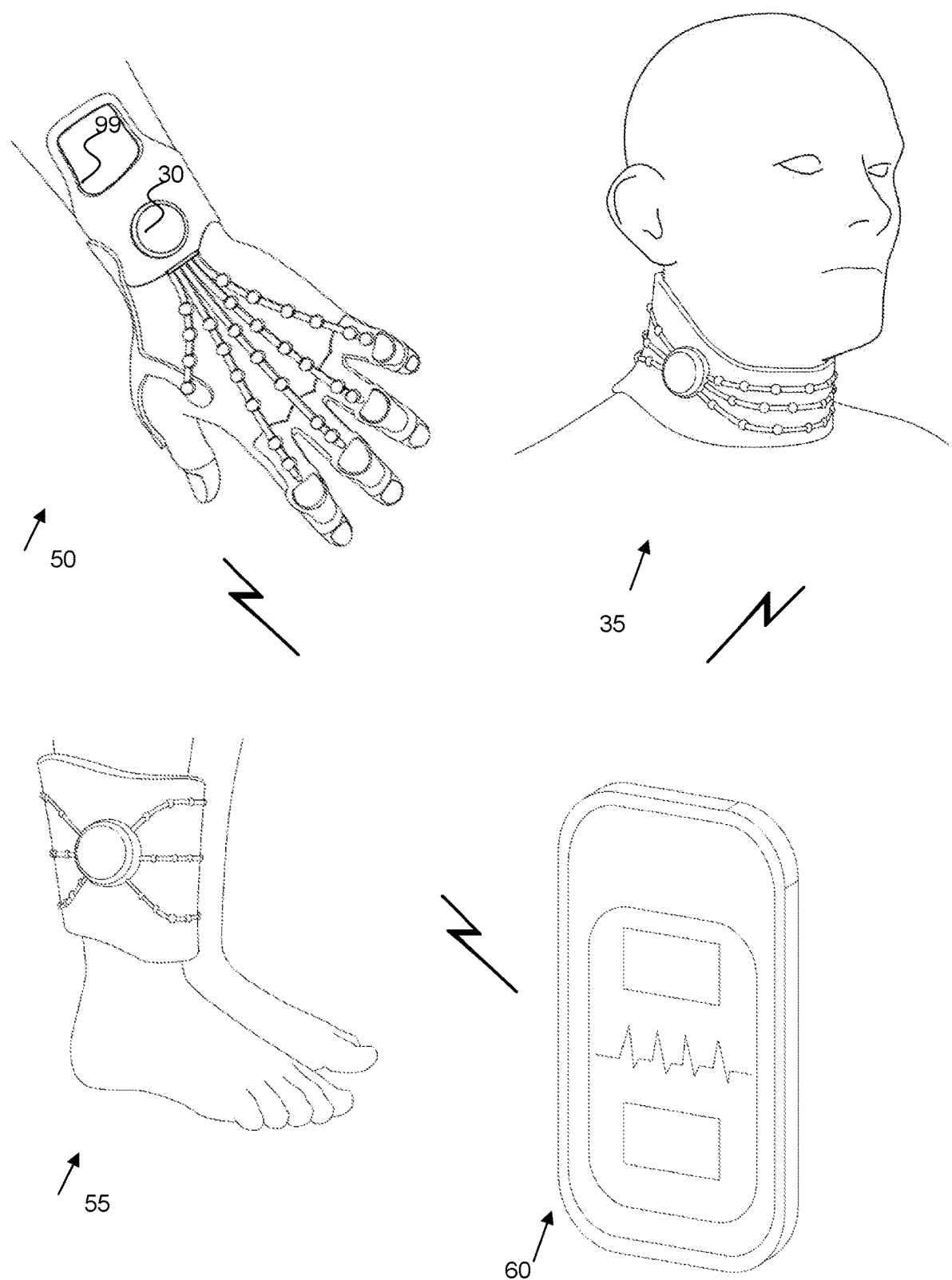
FIG. 10 is a depiction of a cell phone wireless telemetry and communication between the intelligent stop shaking device, system and computer program in accordance with an embodiment of the present disclosure.

FIG. 10 is a depiction of a cell phone wireless telemetry and communication between the intelligent stop shaking device, system and computer program in accordance with an embodiment of the present disclosure. The depiction includes the flexible substrate anklet wrap 45, the hand glove 50, the neck device 35 and a cell phone 60. The mini gyroscopes comprise miniaturized electro-mechanical gyroscopes and accelerometer elements made using microfabrication techniques (MEMS). Also an electronic touch display 99 is in communication with the controller 30, the display configured for an input and output of processed bodily functions and device status. A communications module and protocol thereof are included for wireless telemetry and communication with a cell phone 60. Additionally, sensors are included which are configured to sense, monitor, record and communicate bodily functions.

The intelligent shaking inhibiting devices, system and method will send data to a cell phone or another remote electronic device including time domain and relevance to trembling and shaking frequency, degree of trembling and shaking. This telemetry capability allows a user and patient of the disclosure to track episodes and use graphics and memory functions to manage their health care and ablation of their trembling and shaking. Applications are also included in embodiments which allow the user and patient to program response to tremors and shaking episodes via predetermined inhibiting intensity to allow health care management during sleep.

Figure 11:
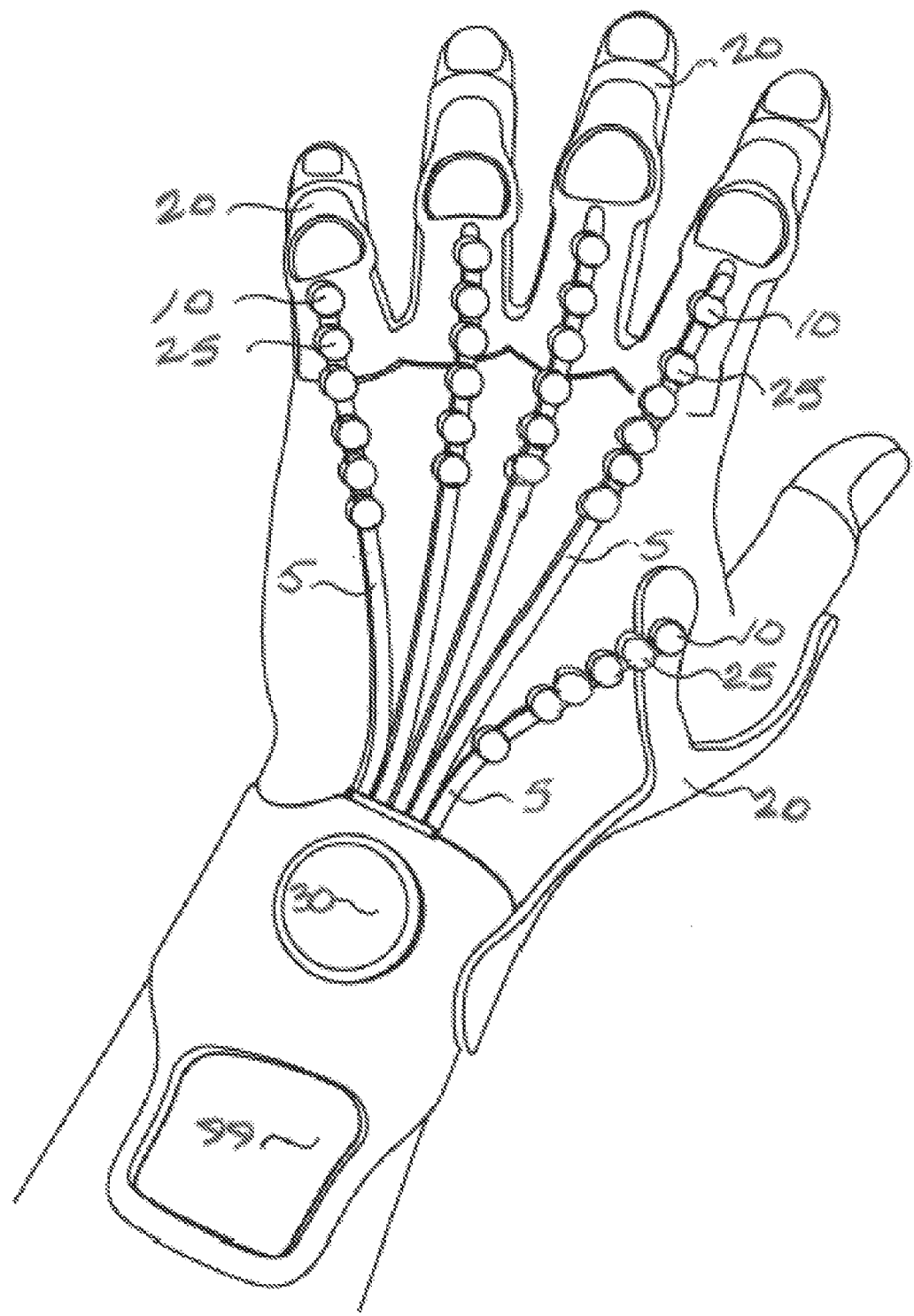
FIG. 11 is a depiction of finger accumulated mini gyroscopes and mini accelerometers in accordance with an embodiment of the present disclosure.

FIG. 11 is a depiction of finger accumulated mini gyroscopes and mini accelerometers in accordance with an embodiment of the present disclosure. The six total MG and MA devices on the five digital tracks 5 are accumulated near the end of a respective track by an action of the user while wearing the glove. The accumulated devices concentrate shaking control near the fingers as opposed to a distributed control or an accumulated control near the wrist. Reference numbers depicted call out similar limitations to reference numbers of other drawings herein.

Figure 12:
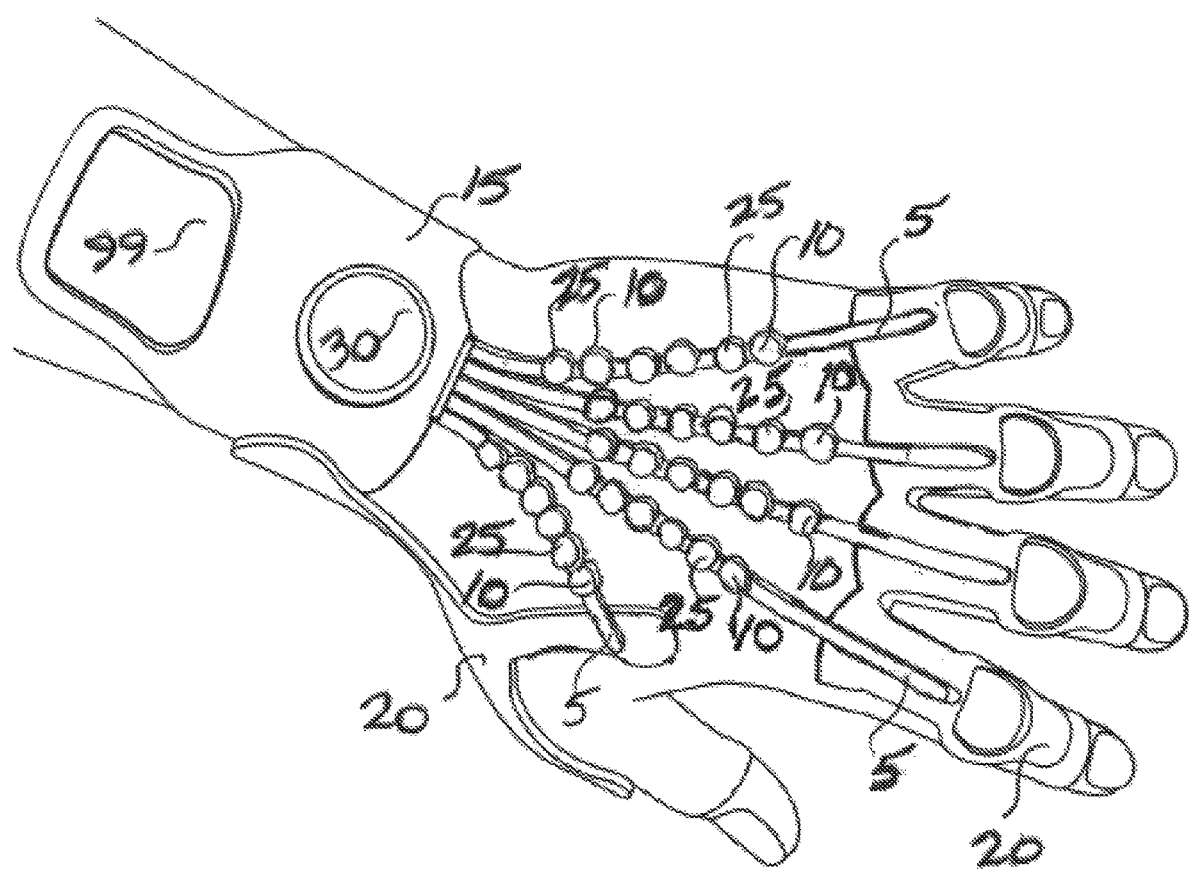
FIG. 12 is a depiction of wrist accumulated mini gyroscopes and mini accelerometers in accordance with an embodiment of the present disclosure.

FIG. 12 is a depiction of wrist accumulated mini gyroscopes and mini accelerometers in accordance with an embodiment of the present disclosure. The six total MG and MA devices on the five digital tracks 5 are accumulated near the end of a respective track by an action of the user while wearing the glove. The accumulated devices concentrate shaking control near the wrist as opposed to a distributed control or an accumulated control near the fingers. Reference numbers depicted call out similar limitations to reference numbers of other drawings herein.

Feedback control is effectuated by the detection by sensors of a difference (the "error signal") between the performance of a device and a model of the intended performance for that device in the particular circumstances of its application. The control section is designed to provide operating instructions to the "effectors" that cause the error signal to be minimized.

Much of feedback system design has to do with stabilization of feedback systems. It is axiomatic that the error signal will be zero during intended operation, but paradoxically this condition will deprive the control mechanism of a meaningful input. Controllers are therefore made sensitive to subtle changes in the rate of change of the sensor signals, and the parameters of permissible operation are adjusted to allow for some error signal, whether constant or dynamically changing.

In the case of IStopShaking the sensors are miniature accelerometers (MAs) and the effectors are mini-gyroscopes (MGs), with adjustable orientation of axes and rotational velocity. Both devices are mounted fairly tightly to the body of the user, so there can be no meaningful difference between their relative positions or their accelerations.

Mechanical gyroscopes operate through the phenomenon of precession—a force exerted on the rotating mass results in a force at right angles with the applied force and the axis of rotation. When the precessional force is resisted, this resistance is translated back to resistance to the externally applied force. In this way mechanical gyros are used to exert a force which resists forces of "ablation acceleration."

In the disclosure, each mini-gyroscope (MG) is composed of a pair of gyros, each with its rotational axis at a 90 degree angle with respect to the other. The effective force generated by such a combination of gyros, analyzed as a single gyro, is the vector combination of the forces exerted by each of the two gyros.

Since gyroscopic force is proportional to angular momentum (which itself is proportional to angular velocity), the resultant vector of force is controlled in both magnitude and direction by the relative angular velocities of the two gyros.

Precessional force produced by a gyroscope cannot exist in the direction of the axis of the gyroscope's rotation—it is confined to a plane normal to the rotational axis. With two gyroscopes fixed at right angles to each other the resultant precessional vector exists within a sphere and takes any spherical angle relative to the intersection point of the two axes.

Such a point of intersection, however, cannot exist physically since the two gyroscopes must be displaced from each other—this will translate into a moment ("twisting force") force of rotation as a necessary component of the precessional resultant. The mountings of the two gyroscopes are therefore capable of resisting this moment for the expected external forces.

Muscular forces in the body are exerted along single axes, due to the structure of muscles and tendons, and the bone structure on which these forces operate. Once can move one's finger in a circle, but it cannot lengthen and shorten, whether through intention or through ablation. The mounting locations of MG pairs are optimized by taking this fact into account.

MAs are mounted where motion is possible and need not be duplicated where motion is constrained. The signals produced by the MA are "filtered" through digital signal processing techniques to extract the first and second derivatives of acceleration. Since ablative effects are usually of higher acceleration both in magnitude and frequency of oscillation, these are extracted through calculation and a resisting force calculated.

Using techniques of feedback control, the repetitive ablative movements are anticipated while ignoring the slowly-varying intentional movements—the higher derivatives of the acceleration become of great importance in assessing the need for change of angular velocity necessary to counter the ablative forces.

In the design of servomechanisms of the disclosure, it is determined an acceptable level of error, which translates into an acceptable level of ablative shaking with minimal suppression of intentional motion. Limits to the effectiveness of the control system depend upon many other factors—most notably the time response of the effectors and sensors. Development of MGs is driven by these requirements as uncovered through research in the field of kinesiology.

Figure 13A:
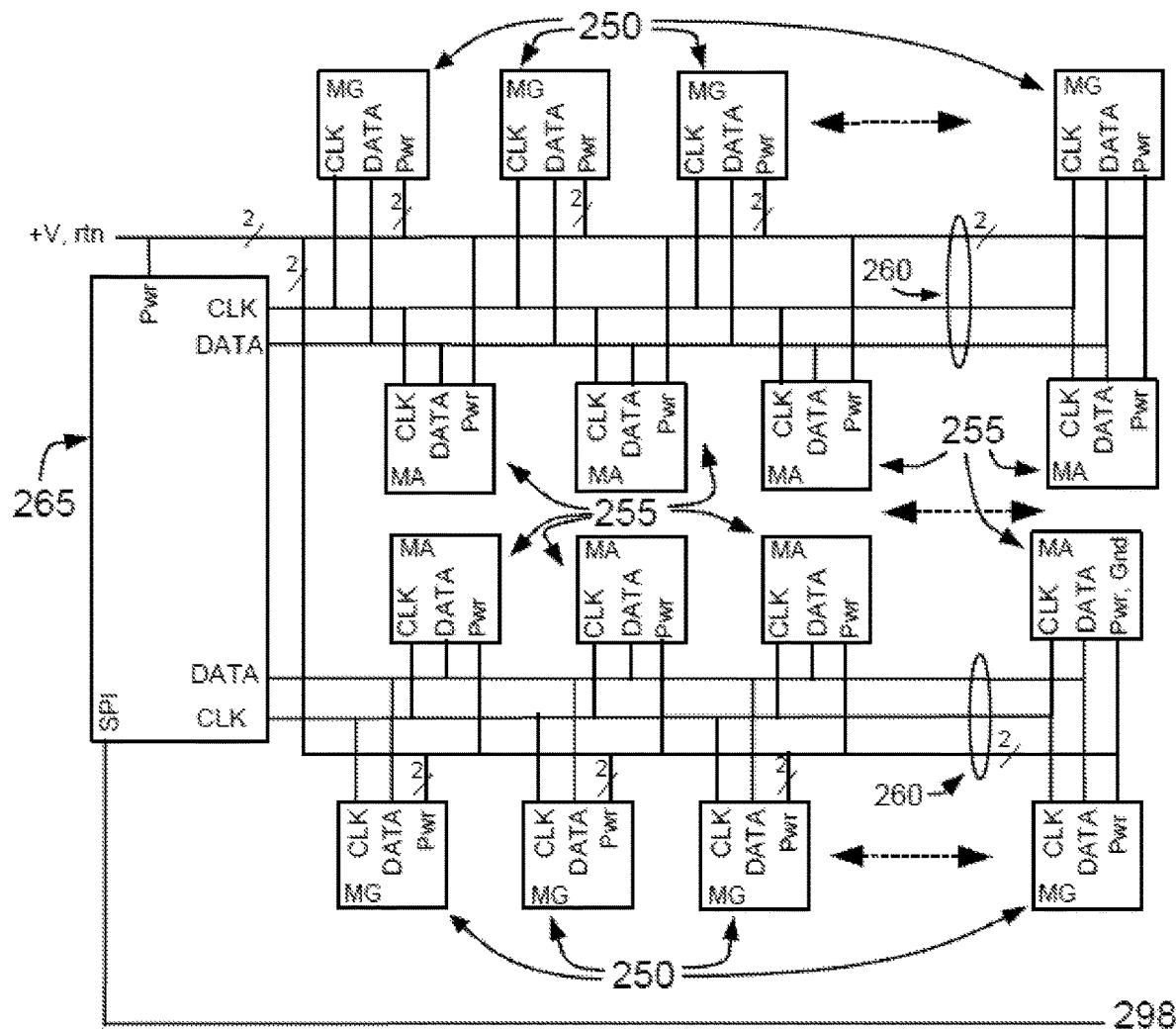
FIG. 13A is a block diagram describing the electrical interconnection of elements comprising the controller for suppression of ablative movement in accordance with an embodiment of the disclosure.

FIG. 13A is a block diagram describing the electrical interconnection of elements comprising the controller for suppression of ablative movement in accordance with an embodiment of the disclosure. It consists of three sections. The present section shows the connection of miniature gyroscopes 250 and miniature accelerometers 255 along tracks 260, which contain conductors for power and return power (shown as a two-conductor channel), clock and data for a two-wire serial addressable communication protocol such as the Philips I2C protocol. Such protocols can transmit data at a rate of 1 Mbit per second. Two tracks 260 are shown with associated MGs and MAs—the tracks are extended beyond the number of MAs and Mgs shown as indicated by the broken line arrows—these indicate the presence of more pairs of MAs and MGs. A serial inter-processor communication bus 298 is shown which connects to the second processor in FIG. 7C. This bus may use a serial point-to-point high speed protocol similar to SPI (Serial Peripheral Interface is a bus used to send data between microcontrollers and small peripherals including registers and sensors using separate clock and data lines and select line) in order to effect transmission between the two processors at maximum speed.

Figure 13B:
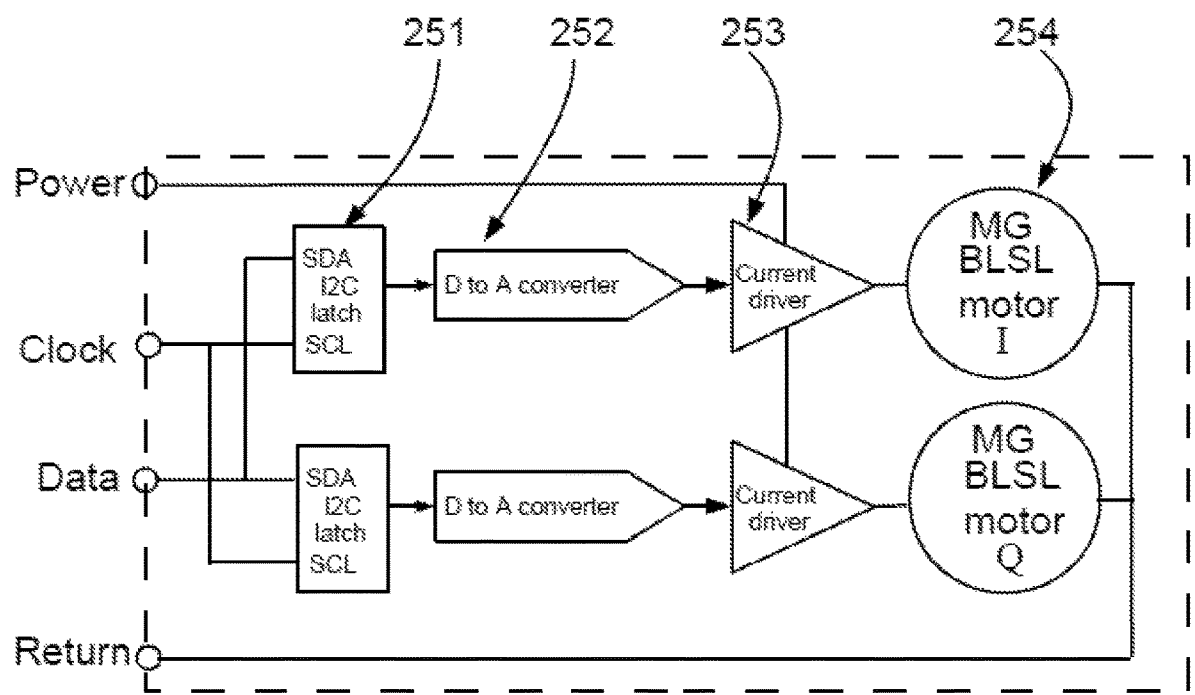
FIG. 13B shows a detail of one MG unit 250, comprising two identical data channels and two gyro motors in accordance with an embodiment of the disclosure.

FIG. 13B shows a detail of one MG unit 250, comprising two identical data channels and two gyro motors in accordance with an embodiment of the disclosure. The motors are mounted rigidly in a 90 degree orientation relative to each other, in order to produce a resultant force vector which can be controlled in direction and magnitude by the relative rotational velocity of the motors labeled MG BLSL motor I and BMG BLSL motor Q. I and Q are standard terminologies in vector operation where I represents "In-phase" and Q represents "Quadrature phase" elements. The quadrature phase relationship here is determined by the 90 degree angular offset between the two rotational axes of the gyros. Each identical data channel comprises a high speed serial receiver 251 which can receive and latch digital data values transmitted over a serial addressable communication protocol. The latched data output is applied to the inputs of digital to analog converter 252, which in turn provides an analog signal to a current driver 253. The output of the current driver drives the gyro motor 254 of the I or Q channel. Through the inclusion of the latch feature these MGs will spin at the commanded rate until a different value is communicated from the Clock and Data inputs and the contents of the latches are changed.

Figure 13C:
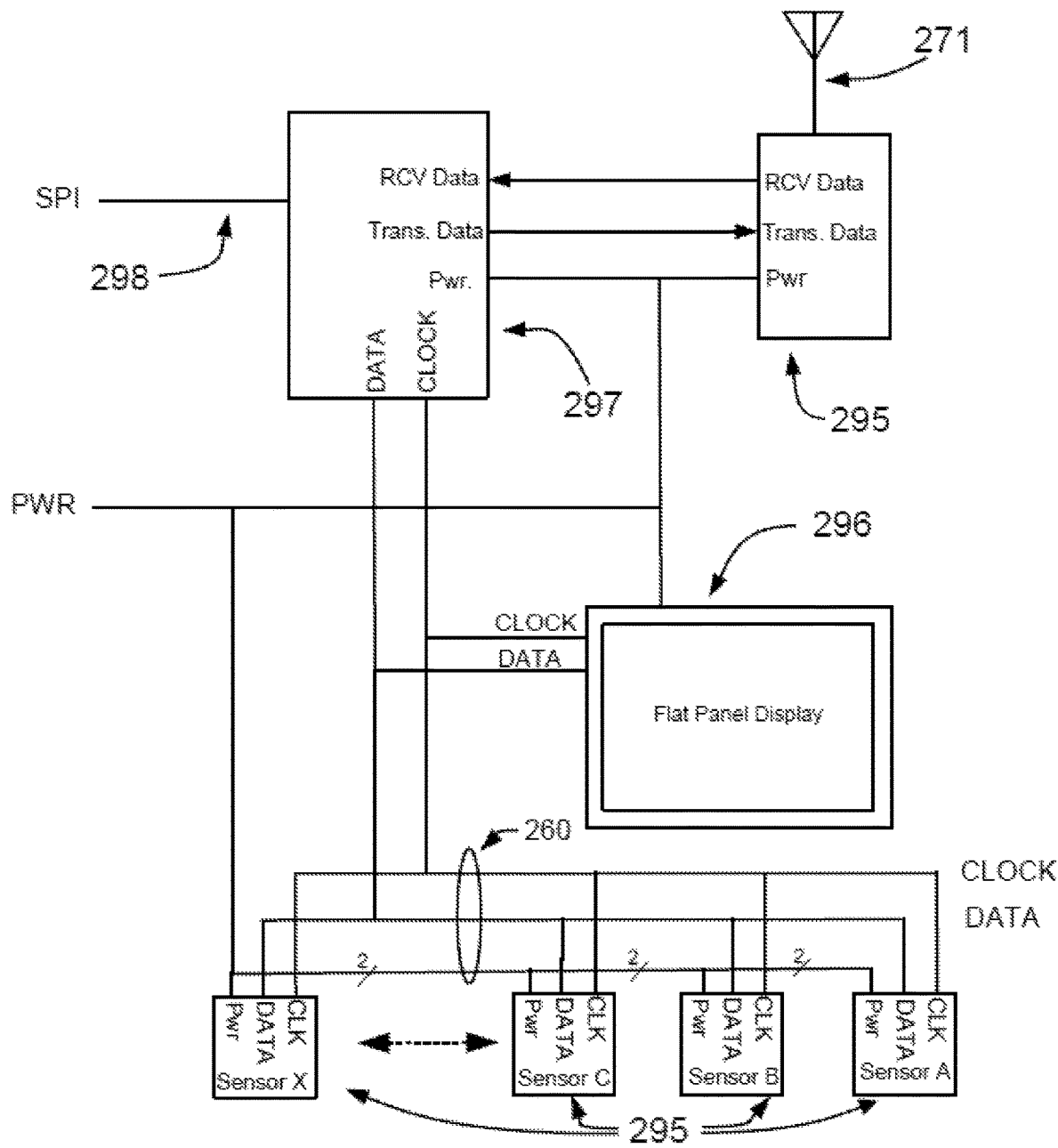
FIG. 13C shows the secondary processor 297 which is connected to the primary processor 265 by the inter-processor communication bus 298 in accordance with an embodiment of the disclosure.

FIG. 13C shows the secondary processor 297 which is connected to the primary processor 265 by the inter-processor communication bus 298 in accordance with an embodiment of the disclosure. The secondary processor 297 performs multiple functions under control of its internal firmware. One such function is the control of and communication through a wireless Bluetooth module 295, having antenna 271 and communicating with processor 297 through serial high-speed channels here labeled RCV Data and Trans. Data. This module enables communication with an external iPhone or similar "smart phone", and through the phone to the Internet and external computers.

Another function is the control and data presentation through a flat-panel miniature display module 296. This module may be an OLED display whose picture elements emit light, which are used in many wearable devices at present. The display module can also be sensitive to touch and report touch events to the secondary processor allowing the user to control aspects of the operation of the system. Communication between the secondary processor 297 and display module 296 is shown as performed through a high-speed serial addressable channel such as I2C, which is part of track 260.

Along this track are the sensors 295 (here shown as sensors a through X). These sensors read both biometric data (heart rate body temperature, pulse oximetry, blood flow as well as others) and environmental data (ambient temperature, barometric pressure, radiation influx as examples) which may prove useful in predicting, evaluating or controlling the performance of the ablation-suppressing activity or which may be useful in interpreting the results telemetered to the external smart phone. The neck, wrist and leg wraps will each have the complement of two processors 265 and 297, but only the wrist wrap will carry the flat panel display and the processors in that wrap can provide the supervisory functions of the whole system if desired.

Figure 14A:
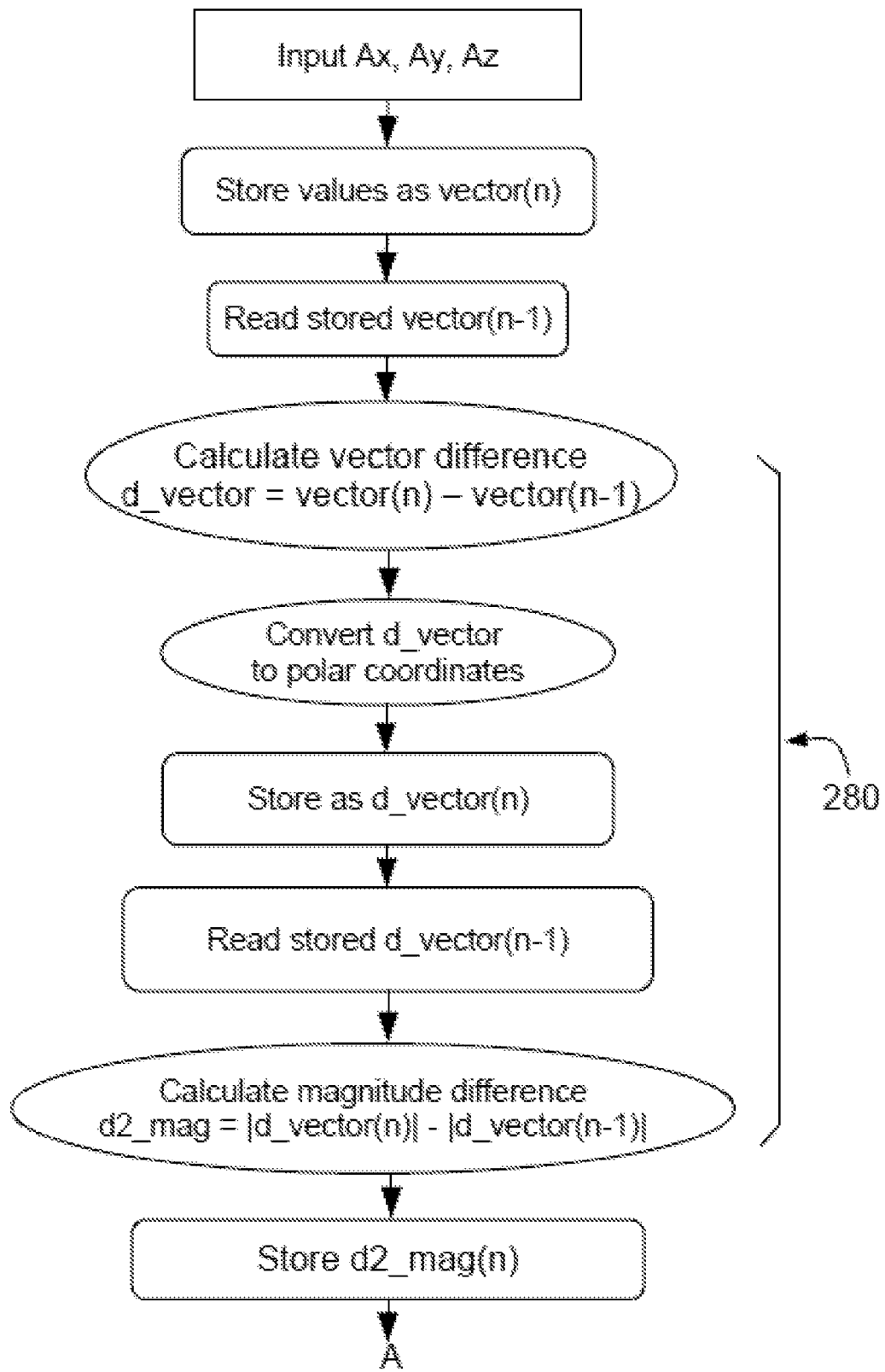
FIG. 14A is a flow chart of a method of intelligently inhibiting shaking in accordance with an embodiment of the present disclosure.

FIG. 14A is a flow chart of a method of intelligently inhibiting shaking in accordance with an embodiment of the present disclosure. It is shown as the following three drawings. The present depiction shows one sequence of program execution for one accelerometer. The program runs under a higher-level scheduling program which may sequence scans and analyses as appropriate to regulate ablation at different locations and different times. The method includes reading values from the three axes of each accelerometer (Ax, Ay, Az) and comparing the values with those taken in the previous sample from the same accelerometer—the current sample index pointer value is labeled (n) and the previous sample index pointer value is labeled (n−1). Sample n is stored as (vector_n). A difference vector is calculated from the two sets of three Cartesian acceleration values and the difference vector is converted to polar coordinates (magnitude and angle). The magnitude of the difference vector is stored as (d_vector) in an array and is then compared with the previous (n−1) difference vector. The difference between the two vector magnitudes is calculated and stored as the second derivative of the acceleration vector (d2_mag).

Figure 14B:
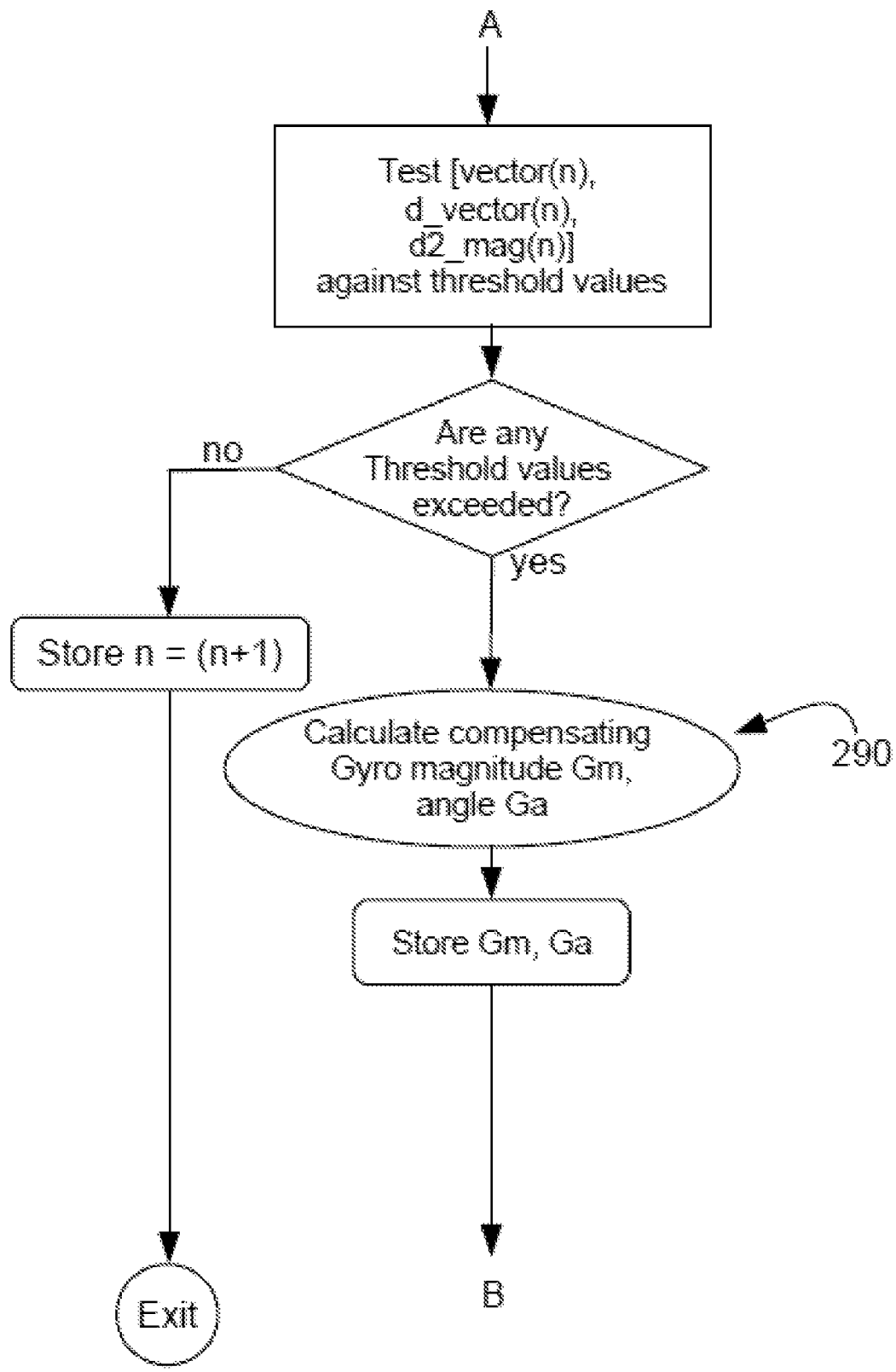
FIG. 14B shows vector(n), d_vector(n) and d2_mag(n) compared with preset threshold values which delineate intentional movement from ablation movements in accordance with an embodiment of the disclosure.

FIG. 14B shows vector(n), d_vector(n) and d2_mag(n) compared with preset threshold values which delineate intentional movement from ablation movements in accordance with an embodiment of the disclosure. If the test indicates normal motion ("no" on the test) then the index pointer n is incremented and the software exits to return control to the higher level program. If ablation is detected ("yes" on the test) then the data are used to calculate the necessary angle and magnitude (Ga and Gm) to allow the appropriate gyroscope to provide compensating force. These values are stored and output to the appropriate gyroscope.

Figure 14C:
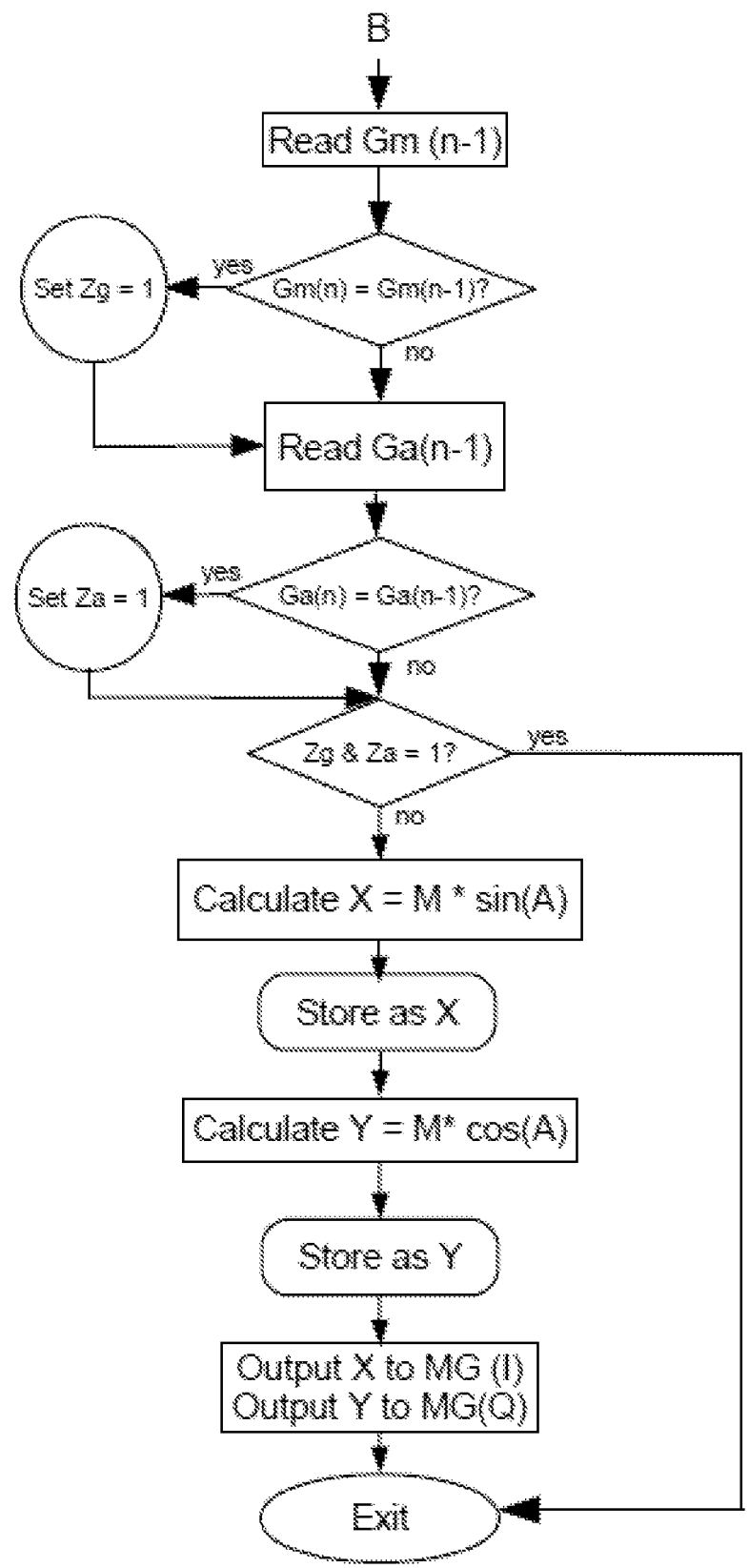
FIG. 14C shows the process through which the values Gm and Ga are converted to Cartesian values to drive the two miniature gyros MG(I) and MG(Q) which produce the equivalent resultant gyro acceleration and axis direction in accordance with an embodiment of the disclosure.

FIG. 14C shows the process through which the values Gm and Ga are converted to Cartesian values to drive the two miniature gyros MG(I) and MG(Q) which produce the equivalent resultant gyro acceleration and axis direction in accordance with an embodiment of the disclosure. The present disclosure therefore meets the long felt need in the market for a device, system, computer program and method for the management and ablation of involuntary shaking, trembling and spasmodic events including seizures. The present disclosure also provides electronic means for the management of many such intelligent no shake devices on all appendages of a patient through a central or distributed application and wireless management including personal digital devices and the internet cloud.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

While the forgoing examples are illustrative of the principles of the present disclosure in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the disclosure be limited, except as by the specification and claims set forth herein.

What is claimed is:

1. A shaking inhibiting device, comprising:
    a plurality of parallel tracks comprising semi rigid connective material disposed on a flexible substrate wrap, the parallel tracks configured to provide a semi rigid route for and an inter placement of a mini gyroscope device and a mini accelerometer device, wherein the plurality of parallel tracks comprise a first end adapted to a control junction and a second end adapted to a finger portion of a user;
    a plurality of the mini gyroscope devices and a means for driving the plurality of mini gyroscope devices accumulated in series at any area along the plurality of parallel tracks between the first and second ends via the user's action(s), the mini gyroscope devices configured to be routed along the parallel tracks and spin at a variable angular momentum;
    a plurality of mini accelerometer devices inter placed between the mini gyroscope devices along the parallel tracks between the first and the second ends, the accelerometer devices configured to measure shaking and purposeful movement of portions of the flexible substrate wrap and provide feedback on shaking ablation; and
    a digital processing circuit configured to be in communication with the plurality of min gyroscope devices and the mini accelerometer devices to control the variable angular momentum and a spin axis of the mini gyroscope devices to ablate shaking relative to purposeful movement of portions of the substrate wrap based on the accelerometer feedback via differentiation of shaking from purposeful movement from a first and a second derivative of acceleration of at least two vector magnitudes.

2. The shaking inhibiting system of claim 1, wherein the parallel tracks are solid and allow the mini gyroscope devices and the accelerometer devices travel thereon according to an accumulation movement of the user.

3. The shaking inhibiting device of claim 1, wherein the means for driving the plurality of mini gyroscope devices includes a plurality of brushless slot DC (direct current) motors configured to drive the variable angular momentum and the spin axis of the gyroscope devices in communication with the digital processing circuit.

4. The shaking inhibiting device of claim 1, wherein the digital processing circuit incorporates the feedback on shaking ablation provided by both a magnitude and a direction of relative angular velocities of the mini gyroscope devices rotating at ninety degree angles with respect to each other.

5. The shaking inhibiting device of claim 1, further providing a flexible wrap configured as a substrate for the plurality of mini gyroscope devices and the plurality of parallel tracks and one or more control junctures, the substrate and portions comprising a hand glove, a necklace and an anklet.

6. A shaking inhibiting system, comprising:
   a plurality of parallel tracks each configured to join a plurality of mini gyroscopes in series, the parallel tracks joined at one or more control junctures and disposed on a flexible substrate wrap, wherein the plurality of parallel tracks comprise a first end adapted to a control junction and a second end adapted to a finger portion of a user;
   a plurality of the mini gyroscopes and a means for driving the plurality of mini gyroscopes accumulated in series in any area on each of the parallel tracks between the first and the second ends via the user's action(s), the mini gyroscopes configured to spin about an axis relative to the parallel tracks at a variable angular momentum;
   a plurality of mini accelerometers configured to measure shaking and purposeful movement of portions of the flexible substrate wrap and provide feedback on shaking ablation; and
   a digital processing circuit configured to be in communication with the plurality of min gyroscope devices and the mini accelerometer devices to control the variable angular momentum and the spin axis of the mini gyroscopes to ablate shaking relative to purposeful movement of portions of the substrate wrap based on accelerometer feedback via differentiation of shaking from purposeful movement from a first and a second derivative of acceleration of at least two vector magnitudes.

7. The shaking inhibiting system of claim 6, wherein the flexible substrate wrap comprises a hand glove with finger and thumb portions and finger and thumb parallel tracks comprising a control juncture adjacent a wrist of the glove.

8. The shaking inhibiting system of claim 6, wherein the flexible substrate wrap further comprises an anklet with three parallel tracks configured to circumnavigate an ankle.

9. The shaking inhibiting system of claim 6, wherein the flexible substrate wrap further comprises a bracelet with three parallel tracks circumnavigating a neck.

10. The shaking inhibiting system of claim 6, wherein at least one controller portion is disposed at one control juncture thereof and another controller portion is disposed at another juncture.

11. The shaking inhibiting system of claim 6, wherein the parallel tracks are solid and allow the mini gyroscopes and the accelerometers to travel thereon according to an accumulation movement of the user.

12. The shaking inhibiting system of claim 6, further comprising an electronic touch display in communication with the controller, the display configured for an input and output of processed bodily functions and device status.

13. The shaking inhibiting system of claim 6, further comprising a communications module and protocol thereof for wireless telemetry and communication with a cell phone.

14. The shaking inhibiting system of claim 6, further comprising sensors configured to sense, monitor, record and communicate bodily functions.

15. A method for inhibiting shaking, the method comprising:
   providing a plurality of parallel tracks comprising semi rigid connective material on a flexible substrate wrap, each track configured to join a plurality of mini gyroscopes in series, the parallel tracks joining one or more control junctures disposed on the flexible substrate wrap, wherein the plurality of parallel tracks comprise a first end adapted to a control junction and a second end adapted to a finger portion of a user;
   providing a plurality of mini gyroscope devices and a means for driving the plurality of mini gyroscope devices accumulated in series on any area on each of the parallel tracks between the first and the second ends via the user's action(s), the mini gyroscopes spinning about an axis relative to the parallel tracks at a variable angular momentum;
   providing a plurality of mini accelerometers for measuring shaking and purposeful moving of portions of the flexible substrate wrap and providing feedback on shaking ablation; and
   providing a digital processing circuit configured to be in communication with the plurality of mini gyroscope devices and the mini accelerometer devices to control the variable angular momentum and the spin axis of the mini gyroscopes to ablate shaking relative to purposeful movement of portions of the substrate wrap based on accelerometer feedback.

16. The method for inhibiting shaking of claim 15, wherein the means for driving the plurality of mini gyroscope devices includes a plurality of brushless slot DC (direct current) motors configured to drive the variable angular momentum and the spin axis of the gyroscope devices in communication with the digital processing circuit.

17. The method for inhibiting shaking of claim 15, further comprising the digital processing circuit setting the spin axis of the mini gyroscopes equal to a direction of the purposeful movement determined by the accelerometer output.

18. The method for inhibiting shaking of claim 15, further comprising incorporating feedback to the digital processing circuit on shaking ablation by both a magnitude and a direction of relative angular velocities of the mini gyroscope devices rotating at ninety degree angles with respect to each other.

19. The method for inhibiting shaking of claim 15, further comprising a plurality of digital processing circuits configured for controlling each of a necklace control juncture, an anklet control juncture and a hand glove control juncture.

* * * * *